US010732188B2

(12) United States Patent
Hess et al.

(10) Patent No.: US 10,732,188 B2
(45) Date of Patent: Aug. 4, 2020

(54) NT-PROANP AND NT-PROBNP FOR THE DIAGNOSIS OF STROKE

(71) Applicant: Roche Diagnostics Operations, Inc., Indianapolis, IN (US)

(72) Inventors: Georg Hess, Mainz (DE); Andrea Horsch, Lucerne (CH); Dietmar Zdunek, Tutzing (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/291,676

(22) Filed: May 30, 2014

(65) Prior Publication Data
US 2014/0274793 A1 Sep. 18, 2014

Related U.S. Application Data

(63) Continuation of application No. PCT/EP2012/073897, filed on Nov. 29, 2012.

(30) Foreign Application Priority Data

Dec. 1, 2011 (EP) .................................. 11191579

(51) Int. Cl.
*A61K 38/00* (2006.01)
*C12Q 1/68* (2018.01)
*G01N 33/567* (2006.01)
*G01N 33/74* (2006.01)
*G01N 33/68* (2006.01)

(52) U.S. Cl.
CPC ......... *G01N 33/74* (2013.01); *G01N 33/6893* (2013.01); *G01N 33/6896* (2013.01); *G01N 2333/58* (2013.01); *G01N 2800/2871* (2013.01); *G01N 2800/50* (2013.01)

(58) Field of Classification Search
None
See application file for complete search history.

(56) References Cited

U.S. PATENT DOCUMENTS

| 5,744,305 | A | 4/1998 | Fodor et al. |
| 2005/0181386 | A1 | 8/2005 | Diamond et al. |
| 2009/0275059 | A1 | 11/2009 | Nomura et al. |
| 2010/0255594 | A1 | 10/2010 | Hess et al. |

FOREIGN PATENT DOCUMENTS

| EP | 1731910 A1 | 12/2006 |
| EP | 1882945 A1 | 1/2008 |
| EP | 1901072 B1 | 11/2009 |
| WO | 2002/083913 A1 | 10/2002 |
| WO | 2002/089657 A2 | 11/2002 |
| WO | 2003/016910 A1 | 2/2003 |
| WO | 2004/059293 A3 | 7/2004 |
| WO | 2005/095642 A1 | 10/2005 |
| WO | 2006/077265 A1 | 7/2006 |
| WO | 2006/087373 A1 | 8/2006 |
| WO | 2006/131529 A1 | 12/2006 |
| WO | 2007/042165 A1 | 4/2007 |
| WO | 2007/110359 A1 | 10/2007 |
| WO | 2010/046136 A1 | 4/2010 |
| WO | 2010/086697 A1 | 8/2010 |
| WO | 2012/080379 A1 | 6/2012 |

OTHER PUBLICATIONS

Adams, Harold P., Jr. et al., "Guidelines for the Early Management of Adults With Ischemic Stroke," Stroke, 2007, pp. 1655-1711, vol. 38.
Fauci, Anthony S. et al., Editors, "Cerebrovascular Diseases," Harrison's Principles of Internal Medicine, 17th Edition, 2008, Chapter 364, pp. 2513-2536, The McGraw-Hill Companies, Inc., USA.
Naruse, Shoji et al., "Effects of Atrial Natriuretic Peptide on Ischemic Brain Edema in Rats Evaluated by Proton Magnetic Resonance Method," Stroke, 1991, pp. 61-65, vol. 22.
Van Der Worp, H. Bart and Van Gijn, Jan, "Acute Ischemic Stroke," The New England Journal of Medicine, 2007, pp. 572-579, vol. 357.
International Search Report dated Jul. 2, 2013 in Application No. PCT/EP2012/073897, 5 pages.
Estrada, Vicente et al., "High Plasma Levels of Endothelin-1 and Atrial Natriuretic Peptide in Patients With Acute Ischemic Stroke," American Journal of Hypertension, 1994, pp. 1085-1089, vol. 7, No. 12.
Garcia-Berrocoso,Teresa et al., "Biomarks in Cardioembolic Stroke," Current Cardiology Reviews, 2010, pp. 194-201, vol. 6.
Giuffrida, Rosario et al., "Immunohistochemical Modifications of Vasoactive Neuropeptides and Excitatory Amino Acids in the Nervous Tissue of the Mongolian Gerbil After Transient Cerebral Ischemia," International Journal of Developmental Neuroscience, 1999, pp. 90-107, vol. 17, No. 2.
Magga, Jarkko et al., "Atrial natriuretic peptide, B-type natriuretic peptide, and serum collagen markers after acute myocardial infarction," Journal of Applied Physiology, 2004, pp. 1306-1311, vol. 96.
Mäkikallio, A. M. et al., "Natriuretic Peptides and Mortality After Stroke," Stroke, 2005, pp. 1016-1020, vol. 36.

(Continued)

*Primary Examiner* — Olga N Chernyshev
(74) *Attorney, Agent, or Firm* — Roche Diagnostics Operations, Inc.

(57) ABSTRACT

The present invention relates to a method for diagnosing a transitory ischemic attack (TIA) in a subject who is suspected to have exhibited a transitory ischemic attack, but who did not exhibit a stroke. The method is based on the determination of the amount of NT-proANP in a sample from said subject. Moreover, the present invention is directed to a method for diagnosing an acute cerebral ischemic event in a subject based on the determination of the amounts of NT-proBNP and NT-proANP in a sample from a subject. The method further comprises the step of calculating a ratio of the amounts of NT-proBNP and NT-proANP. Further envisaged by the present invention are kits and devices adapted to carry out the method of the present invention.

5 Claims, No Drawings

(56) References Cited

OTHER PUBLICATIONS

Rodriquez-Yáñez, Manuel et al., "High serum levels of pro-brain natriuretic peptide (pro BNP) identify cardioembolic origin in undetermined stroke," Disease Markers, 2009, pp. 189-195, vol. 26.

Sato, Yoshihiro et al., "Plasma Concentrations of Atrial Natriuretic Peptide in Cardioembolic Stroke with Atrial Fibrillation," The Kurume Medical Journal, 1995, pp. 71-77, vol. 42.

Shibazaki, Kensaku et al., "Plasma Brain Natriuretic Peptide Can be a Biological Marker to Distinguish Cardioembolic Stroke from Other Stroke Types in Acute Ischemic Stroke," Internal Medicine, 2009, pp. 259-264, vol. 48.

Dambinova, Svetlana A. et al., Multiple Panel of Biomarkers for TIA/Stroke Evaluation, Circulation, 2001, pp. 1181-1182, vol. 103.

Wachter, Rolf et al., Natriuretic Peptides for the Detection of Paroxysmal Atrial Fibrillation in Patients with Cerebral Ischemia—the Find-AF Study, PLoS One, 2012, e34351, 7 pps., vol. 7, Issue 4.

Wang, Thomas J. et al., Plasma Natriuretic Peptide Levels and the Risk of Cardiovascular Events and Death, The New England Journal of Medicine, 2004, pp. 655-663, vol. 350.

Ala-Kopsala, Minna et al., Molecular Heterogeneity Has a Major Impact on the Measurement of Circulating N-Terminal Fragments of A- and B-Type Natriuretic Peptides, Clinical Chemistry, 2004, pp. 1576-1588, vol. 50, No. 9.

Bonow, Robert O., New Insights Into the Cardiac Natriuretic Peptides, Circulation, 1996, pp. 1946-1950, vol. 93.

Hunt, Sharon A. et al., ACC/AHA Guidelines for the Evaluation and Management of Chronic Heart Failure in the Adult: Executive Summary, Journal of the American College of Cardiology, 2001, pp. 2101-2113, vol. 38, No. 7.

Hunt, Sharon Ann et al., ACC/AHA 2005 Guideline Update for the Diagnosis and Management of Chronic Heart Failure in the Adult, Journal of the American College of Cardiology, 2005, pp. e1-e82, vol. 46.

Levey, Andrew S. et al., A More Accurate Method to Estimate Glomerular Filtration Rate from Serum Creatinine: A New Prediction Equation, Annals of Internal Medicine, 1999, pp. 461-470, vol. 130, No. 6.

Nolan, John P. and Sklar, Larry A., Suspension array technology: evolution of the flat-array paradigm, Trends in Biotechnology, 2002, pp. 9-12, vol. 20, No. 1.

Wiggins, A. K. et al., Atrial Natriuretic Peptide Expression is Increased in Rat Cerebral Cortex Following Spreading Depression: Possible Contribution to SD-Induced Neuroprotection, Neuroscience, 2003, pp. 715-726, vol. 118.

Zweig, Mark H. and Campbell, Gregory, Receiver-Operating Characteristic (ROC) Plots: A Fundamental Evaluation Tool in Clinical Medicine, Clinical Chemistry, 1993, pp. 561-577, vol. 39, No. 4.

NT-PROANP AND NT-PROBNP FOR THE DIAGNOSIS OF STROKE

The present invention relates to a method for diagnosing a transitory ischemic attack (TIA) in a subject who is suspected to have exhibited a transitory ischemic attack, but who did not exhibit a stroke. The method is based on the determination of the amount of NT-proANP in a sample from said subject. Moreover, the present invention is directed to a method for diagnosing an acute cerebral ischemic event in a subject based on the determination of the amounts of NT-proBNP and NT-proANP in a sample from a subject. The method further comprises the step of calculating a ratio of the amounts of NT-proBNP and NT-proANP. The present invention also relates to systems for performing a diagnosis of a TIA and for diagnosing an acute cerebral ischemic event, and to reagents and kits used in performing the methods disclosed herein. Further envisaged by the present invention are kits and devices adapted to carry out the method of the present invention.

Stroke ranks after ischemic heart disease second as a cause of lost disability—adjusted—life years in high income countries and as a cause of death worldwide. If presented early, adverse consequences of stroke can be ameliorated by thrombolysis, in case of late presentation secondary prevention (prevention of secondary stroke) using aspirin and anticoagulation appears the only appropriate method to avoid disease progression.

Transitory ischemic attacks (TIAs) are episodes of stroke symptoms that last only briefly, the standard definition is below 24 h, but most TIAs last below 1 h. The causes of TIA are similar to the causes of ischemic stroke, but because TIAs may herald stroke they are an important risk factor that should be considered separately.

The diagnosis of transitory ischemic attacks (TIA) represents a specific challenge, since symptoms rarely last rarely and then symptoms disappear, leaving the attending physician in uncertainty about the diagnosis and the required workup. Moreover, symptoms are dependent on the region (and the accompanying vessel) affected. Frequently, the arteria cerebri media is affected, associated symptoms include aphasia, weakness of arms or legs contralateral. TIA of the a cerebri anterior might be associated with aphasia, apractnosia, confusion, alexia etc, if the central part of the inferior brain is affected, symptoms might be intention tremor, ataxia dysesthesia etc. Lesions of the medulla might include vertigo, diplopia, nausea and vomiting. Thus, many symptoms might be non-specific. Moreover, since they are only temporarily present, they cannot be verified. Accordingly, the diagnosis of TIA might be difficult and cannot be easily separated from other diseases.

TIA is caused by temporary hypoperfusion and ischemia of localized regions of the brain and the malfunction is caused by reversible functional abnormalities of the brain caused by a local edema resulting in metabolic and ionic disturbances. The diagnosis of TIA is important since persons who had TIA have a significantly increased risk of stroke compared to those without these TIA episodes. The risk of stroke is 4-5% after two days, and 11% after seven days following a TIA. Patients who have had a TIA within the previous 48 hours, with TIA lasting >10 minutes, with atrial fibrillation, and with progressive carotid stenosis and TIAs occurring more than once following a crescendo pattern have the greatest risk of stroke.

NT-proBNP and NT-proANP are well known cardiac markers. NT-proBNP belongs to the group of Brain natriuretic peptides which are known to be released from the brain, however the majority of BNPs originate from the heart. Both NT-proBNP and NT-proANP have been associated with cardioembolic causes of stroke.

The inventors have determined the amounts of NT-proANP and NT-proBNP in a large cohort of TIA and stroke patients. NT-proANP turned out to be a reliable marker for TIA. This observation is advantageous since the diagnosis of TIA is difficult (in particular in contrast to the diagnosis of stroke). Moreover, it was shown that the NT-proANP levels in TIA patients are elevated for a considerable time after TIA. This allows the diagnosis of TIA even days after the TIA.

There is a need for means and methods for diagnosing a transitory ischemic attack in a subject. Accordingly, the technical problem underlying the present invention could be seen as the provision of means and methods for complying with the aforementioned need.

The technical problem is solved by the embodiments characterized in the claims and herein below.

Method for Diagnosing a Transitory Ischemic Attack (TIA)

The present invention relates to a method for diagnosing a transitory ischemic attack (TIA) in a subject who is suspected to have exhibited a transitory ischemic attack, but who did not exhibit a stroke, comprising the determination of the amount of NT-proANP in a sample from said subject.

In an embodiment, the aforementioned method further comprises the comparison of the determined amount of NT-proANP to a reference amount. Thereby, a transitory ischemic attack is diagnosed.

Thus, the present invention, in particular, relates to a method for diagnosing a transitory ischemic attack (TIA) in a subject who is suspected to have exhibited a transitory ischemic attack, but who did not exhibit a stroke, said method comprising the steps of a. determining the amount of NT-proANP in a sample from said subject, and
b. comparing the determined amount of NT-proANP to a reference amount, whereby a transitory ischemic attack is diagnosed.

In some embodiments, it is diagnosed whether the subject has exhibited a transitory ischemic attack, or not, by carrying out the further step of c) diagnosing whether the subject has exhibited a transitory ischemic attack, or not, based on the result of the comparison carried out in step b).

The method of the present invention, preferably, is an ex vivo method. Moreover, it may comprise steps in addition to those explicitly mentioned above. For example, further steps may relate to sample pre-treatments or evaluation of the results obtained by the method. The method may be carried out manually or assisted by automation. Preferably, step (a) and/or (b) may in total or in part be assisted by automation, e.g., by a suitable robotic and sensory equipment for the determination in step (a) or a computer-implemented comparison and/or diagnosis based on said comparison in step (b). More preferably, the method is carried out entirely in an automated manner. In such a case, the diagnostic result which is established in step b) is generated in a suitable output format so that it can be used as an aid for establishing the final clinical diagnosis by, e.g., a medical practitioner.

Accordingly, the present invention also preferably relates to a system for diagnosing a transitory ischemic attack (TIA) in a subject who is suspected to have exhibited a transitory ischemic attack, but who did not exhibit a stroke, comprising a) an analyzer unit configured to contact, in vitro, a portion of a sample from the subject with a ligand comprising specific binding affinity for the marker NT-proANP, b) an analyzer unit configured to detect a signal from the portion of the sample from the subject contacted with the ligand,
c) a computing device having a processor and in operable communication with said analysis units, and
d) a non-transient machine readable media including a plurality of instruction executable by the processor, the instructions, when executed calculate an amount of the marker, and compare the amount of the marker with a reference amount, thereby diagnosing a transitory ischemic attack.

The term "subject" as used herein relates to animals, preferably mammals, and, more preferably, humans. The subject according to the present invention shall be suspected to have exhibited a transitory ischemic attack. Preferably, said subject shall be suspected to have exhibited a transitory ischemic attack within 72 hours, more preferably, within 48 hours, and most preferably within 24 hours before the sample to be tested has been obtained. Accordingly, it shall be diagnosed in accordance with the present invention, whether the test subject has exhibited a TIA, or has not exhibited a TIA, preferably, within 72 hours, more preferably, within 48 hours, and most preferably within 24 hours before the test sample has been obtained.

Preferably, the subject to be tested (as well as the subject from which the reference amount is derived) does not have impaired renal function. How to assess whether a subject exhibits impaired renal function is well known in the art. Renal disorders can be diagnosed by any means known and deemed appropriate. Particularly, renal function can be assessed by means of the glomerular filtration rate (GFR). For example, the GFR may be calculated by the Cockgroft-Gault or the MDRD formula (Levey 1999, Annals of Internal Medicine, 461-470). GFR is the volume of fluid filtered from the renal glomerular capillaries into the Bowman's capsule per unit time. Clinically, this is often used to determine renal function. The GFR was originally estimated (the GFR can never be determined, all calculations derived from formulas such as the Cockgroft Gault formula of the MDRD formula deliver only estimates and not the "real" GFR) by injecting inulin into the plasma. Since inulin is not reabsorbed by the kidney after glomerular filtration, its rate of excretion is directly proportional to the rate of filtration of water and solutes across the glomerular filter. In clinical practice however, creatinine clearance is used to measure GFR. Creatinine is an endogenous molecule, synthesized in the body, which is freely filtered by the glomerulus (but also secreted by the renal tubules in very small amounts). Creatinine clearance (CrCl) is therefore a close approximation of the GFR. The GFR is typically recorded in milliliters per minute (mL/min) The normal range of GFR for males is 97 to 137 mL/min, the normal range of GFR for females is 88 to 128 ml/min. Thus, it is particularly contemplated that the GFR of a subject who does not exhibit impaired renal function is within this range. Moreover, said subject preferably, has a blood creatinine level (in particular a serum creatinine level) of lower than 0.9 mg/dl, more preferably of lower than 1.1 mg/dl and most preferably of lower than 1.3 mg/dl.

In many instances, the subject has risk factors for an acute cerebral ischemic event, in particular for TIA. The term "acute cerebral ischemic event" is described elsewhere herein. Examples of risk factors include coronary artery disease, heart failure, in particular acute heart failure, systolic and/or diastolic cardiac dysfunction, valvular heart disease, and arterial hypertension. Further risk factors are diabetes and obesity. Accordingly, the test subject often shows at least one of these risk factors. In particular, it is envisaged that the test subject (and the reference subject, i.e. the subject from which the reference amount is derived) suffers from coronary artery disease and/or from heart failure.

In many instances, the subject suffers from heart failure. This applies in particular, if a ratio of the amounts of NT-proANP and NT-proBNP is calculated in the context of the method of the present invention (see elsewhere herein). The term "heart failure" is well known in the art. As used herein, the term relates to an impaired systolic and/or diastolic function of the heart being accompanied by overt signs of heart failure. Heart failure referred to herein is chronic heart failure. Most often, it is acute heart failure. The term "acute heart failure refers to a worsening of cardiac function within a maximum of 2 weeks with or, in particular, without pre-existing chronic heart failure.

Heart failure can be classified into various degrees of severity. According to the NYHA (New York Heart Association) classification, heart failure patients are classified as belonging to NYHA classes I, II, III and IV. A patient having heart failure has already experienced structural and functional changes to his pericardium, myocardium, coronary circulation or cardiac valves. He will not be able to fully restore his health, and is in need of a therapeutical treatment. Patients of NYHA Class I have no obvious symptoms of cardiovascular disease but already have objective evidence of functional impairment. Patients of NYHA class II have slight limitation of physical activity. Patients of NYHA class III show a marked limitation of physical activity. Patients of NYHA class IV are unable to carry out any physical activity without discomfort. They show symptoms of cardiac insufficiency at rest.

This functional classification is supplemented by the more recent classification by the American College of Cardiology and the American Heart Association (see J. Am. Coll. Cardiol. 2001; 38; 2101-2113, updated in 2005, see J. Am. Coll. Cardiol. 2005; 46; e1-e82). 4 stages A, B, C and D are defined. Stages A and B are not heart failure ("HF") but are considered to help identify patients early before developing "true" HF. Stages A and B patients are best defined as those with risk factors for the development of HF. For example, patients with coronary artery disease, hypertension, or diabetes mellitus who do not yet demonstrate impaired left ventricular (LV) function, hypertrophy, or geometric chamber distortion would be considered stage A, whereas patients who are asymptomatic but demonstrate LV hypertrophy and/or impaired LV function would be designated as stage B. Stage C then denotes patients with current or past symptoms of HF associated with underlying structural heart disease (the bulk of patients with HF), and stage D designates patients with truly refractory HF.

As used herein, the term "heart failure" refers to stages C and D of the ACC/AHA classification referred to above. In these stages, the subject shows typical symptoms of heart failure. Accordingly, a subject who suffers from heart failure suffers from heart failure stage C or D according to the ACC/AHA classification. If using the NYHA classification herein, the term "heart failure" is classified as NYHA III or IV.

It is further envisaged that the subject to be tested in accordance with the method of the present invention (as well as the reference subject(s)) does not exhibit an acute coronary syndrome (abbreviated "ACS"). The term "ACS" as used herein includes STEMI (ST-elevation myocardial infarction); NSTEMI (non ST-elevation myocardial infarction) and unstable angina pectoris. It is further envisaged that the subject to be tested does not have a history of ACS. Preferably, the subject shall not have suffered from ACS within one week or, more preferably, one month prior to carrying out the method of the present invention (to be more precise, within one month prior to obtaining the sample).

In certain embodiments, the subject does also not suffer from a cardiac circulatory event (in particular when the sample is obtained). The term "cardiac circulatory event", preferably, refers to a sudden deterioration of the function of the heart. Such a deterioration is usually caused by cardiac arrhythmia, transient cardiac arrest or pulmonary embolism. Cardiac arrhythmia can occur in two forms: bradyarrhythmia and tachyarrhythmia. In bradyarrhythmia the frequency of heartbeat is pathologically decreased in comparison to a healthy subject, preferably in bradyarrhythmia the heart rate is lower than 60 beats per minute. The most frequent forms of bradyarrhythmia are sinus bradycardia, sinoatrial block, sinus arrest, sick sinus syndrome and atriventricular block. In tachyarrhythmia the frequency is pathologically increased when compared with a healthy subject, preferably in bradyarrhythmia the heart rate is higher than 100 beats per minute. Most cases of tachyarrhythmia are supraventricular tachycardia with structural cardiovascular disease, atrial fibrillation with the Wolff-Parkinson-White syndrome, atrial flutter with 1:1 atrioventricular conduction and ventricular tachycardia. Pulmonary embolism is caused the occlusion of a pulmonary artery by a blood clot (thromboembolism) or an air bubble (air embolism). Typically, blood clots are formed in the pelvic or lower extremity veins and migrate to the pulmonary arteries where they get stuck. Air embolism is, preferably, caused by a diving accident or by leaky venous catheters. Symptoms of pulmonary embolism include chest pain, dyspnea and hemoptysis (coughing of blood). The pressure in the lung circulation may rise and may cause right ventricular failure. Cardiac circulatory events may as well be determined or confirmed by the hitherto known methods.

The term "transient ischemic attack" (abbreviated as TIA herein) is well known in the art (see W. E. Smith et al, Cerebrovascular Diseases, chapter 364 in Harrison, Principles of Internal Medicine, 17th edition). As used herein, the term, preferably, refers to a transient episode of neurologic dysfunction caused by ischemia without acute infarction and, thus, without tissue death. Thus, in contrast to stroke, a TIA does not lead to irreversible tissue damage due to brain cell death. TIA shares the same underlying etiology as stroke: a disruption of cerebral blood flow (CBF). Moreover, the symptoms of TIA are usually the same as for stroke. Symptoms of TIA and stroke are well known in the art. Moreover, it is well known in the art that they may depend on the region of the brain affected by ischemia (see also below) and that they may vary in severity. Symptoms include temporary loss of vision (amaurosis fugax), difficulties in speaking (aphasia); weakness on one side of the body (hemiparesis), and numbness or tingling (paresthesia), usually on one side of the body. Further symptoms are dysphasia, dysarthria, hemianopia, weakness, ataxia, and neglect. Dizziness, lack of coordination or poor balance are also symptoms related to TIA.

The symptoms of a TIA are short-lived and usually last a few seconds to a few minutes and most symptoms disappear within 60 minutes. Accordingly, the symptoms last only briefly, often less than 24 hours, in particular less than 1 hour.

In general, the subject to be tested in accordance with the aforementioned method did not exhibit a stroke. In some embodiments, the subject shall not have exhibited a stroke within 72 hours, within 48 hours, and, in some embodiments, within 24 hours before the sample to be tested has been obtained. In certain embodiments, the subject shall not have exhibited a stroke within one or two weeks before the test sample has been obtained.

The term "stroke" is well known in the art. The term encompasses ischemic stroke. The term "ischemic stroke" is also well understood by the skilled person (see e.g. Adams et al., Guidelines for the Early Management of Adults With Ischemic Stroke, A Guideline From the American Heart Association/American Stroke Association Stroke Council, Clinical Cardiology Council, Cardiovascular Radiology and Intervention Council, and the Atherosclerotic Peripheral Vascular Disease and Quality of Care Outcomes in Research Interdisciplinary Working Groups in Stroke. 2007; 38:1655 which is herewith incorporated by reference with respect to its entire disclosure content). As used herein, the term refers to cerebral ischemic stroke. Moreover, it refers to a stroke which is caused by reduced blood flow to the brain or parts thereof which leads to a reduced delivery (undersupply) of oxygen to brain cells. A stroke in the context of the methods of the present invention leads to irreversible tissue damage due to brain cell death. Accordingly, the term "stroke", as used herein, does not include TIAs.

Symptoms of stroke are well known in the art. Usually they are they are the same symptoms as disclosed for TIAs above.

Ischemic stroke may be caused by atherothrombosis or embolism of a major cerebral artery, by coagulation disorders or nonatheromatous vascular disease, or by cardiac ischemia which leads to a reduced overall blood flow. The ischemic stroke is usually selected from the group consisting of atherothrombotic stroke, cardioembolic stroke and lacunar stroke. Determination of the type stroke is known to the person skilled in the art and includes different imaging techniques such as echocardiography, electrocardiogram and doppler ultrasound. In many instances, the ischemic stroke is an acute ischemic stroke.

TIA and stroke are result of ischemia and or hypoperfusion of specific or all parts of the brain. Symptoms are dependent on the region (and the accompanying vessel) affected. Frequently the arteria cerebri media is affected, associated symptoms include aphasia, weakness of arms or legs contralateral, TIA of the a cerebri anterior might be associated with aphasia, apractnosia, confusion, alexia etc., if the central part of the inferior brain is affected, symptoms might be intention tremor, ataxia dysesthesia etc. lesions of the medulla might include vertigo, diplopia, nausea and vomiting.

The term "ischemic stroke" does not include hemorrhagic stroke.

Whether a subject suffers or suffered from stroke, in particular from ischemic stroke can be determined by well-known methods. Moreover, symptoms of stroke are well known in the art. Stroke symptoms include sudden numbness or weakness of face, arm or leg, especially on one side of the body, sudden confusion, trouble speaking or understanding, sudden trouble seeing in one or both eyes, and sudden trouble walking, dizziness, loss of balance or coordination.

As set forth above, the subject to be tested in accordance with the aforementioned method shall be suspected to have exhibited a transitory ischemic attack. Preferably, a subject who is suspected to have exhibited a transitory ischemic attack is a subject who has shown symptoms of a TIA. In some embodiments, said subject has shown symptoms of a TIA within a certain window period prior to obtaining the test sample. Often, said subject has shown symptoms of TIA within 72 hours, within 48 hours, and most often within 24 hours before the sample has been obtained. Preferably, however, the test sample shall be obtained not earlier than 1 hour, in particular, not earlier than 2 hours after the end of symptoms of TIA. Further, it is envisaged that the test sample has not been obtained earlier than 4 hours after the end of symptoms of TIA. Also it is envisaged, that the test sample has not been obtained earlier than 6 hours after the end of symptoms of TIA.

It is also envisaged that the subject has shown symptoms of TIA within 12 hours before the sample has been obtained.

By the aforementioned method of the present invention, a TIA shall be diagnosed. The term "diagnosing" as used herein means assessing whether a subject as referred to in accordance with the method of the present invention has exhibited a transitory ischemic attack, or not. In particular, it shall be diagnosed whether the subject has exhibited a transitory ischemic attack, or not within a certain window period before obtaining the sample to be tested. In a preferred embodiment, it shall be diagnosed whether the subject has exhibited a transitory ischemic attack, or not, within 72 hours before the sample has been obtained. In a further preferred embodiment, it shall be diagnosed whether the subject has exhibited a transitory ischemic attack, or not, within 48 hours before the sample has been obtained. In an even further preferred embodiment, it shall be diagnosed whether the subject has exhibited a transitory ischemic attack, or not, within 24 hours before the sample has been obtained. Preferably, the subject does not show symptoms of TIA anymore at the time at which the sample is obtained.

As will be understood by those skilled in the art, the assessment whether a subject as referred to herein has exhibited a TIA, or not, is usually not intended to be correct for 100% of the subjects to be diagnosed. The term, however, requires that the assessment is correct for a statistically significant portion of the subjects (e.g. a cohort in a cohort study). Thus, the method of the present invention, however, at least provides an aid for establishing a final clinical diagnosis. Whether a portion is statistically significant, can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma, urine or serum and, most preferably, blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein. Preferably, said sample is obtained not more than 72 hours after the onset of symptoms of a transitory ischemic attack. More preferably, said sample is obtained not more than 48 hours, and, most preferably, not more than 24 hours after the onset of symptoms of a transitory ischemic attack. Preferably, the subject does not show symptoms of TIA anymore at the time at which the sample is obtained.

The marker NT-proANP (N-terminal pro-atrial natriuretic peptide) is well known in the art (see e.g. Bonow, 1996, Circulation 93: 1946-1950 which is herewith incorporated by reference in its entirety). NT-proANP belongs to the group natriuretic peptides. NT-proANP and is generated by proteolytic cleavage from a precursor molecule, the pre-proANP peptide, resulting in the active hormone ANP (Atrial natriuretic peptide) and the corresponding N-terminal fragment NT-proANP. ANP is synthesized in atrial myocytes. On release the prohormone is split into equimolar amounts of the highly biologically active proANP (amino acids 99 to 126) and NT-proANP (amino acids 1 to 98). The active hormone is involved in the homeostatic control of body water, sodium, potassium and adipose tissue. It is released by muscle cells in the upper chambers of the heart in response to high blood pressure. NT-proANP as used herein refers to human NT-proANP. The term "NT-proANP", also encompasses variants of the aforementioned human NT-proANP polypeptides. Such variants have at least the same essential biological or immunological properties as the aforementioned NT-proANP polypeptide. In particular, they share the same essential biological or immunological properties if they are detectable by the same specific assays referred to in this specification, e.g., by ELISA assays using polyclonal or monoclonal antibodies specifically recognizing the said NT-proANP polypeptides. Examples of particular variants of NT-proANP and NT-proBNP and methods for their measurement are to known (Ala-Kopsala, M., Magga, J., Peuhkurinen, K. et al. (2004): Molecular heterogeneity has a major impact on the measurement of circulating N-terminal fragments of A-type and B-type natriuretic peptides. Clinical Chemistry, vol. 50(9), 1576-1588). Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino acid sequence of the specific NT-proANP polypeptide, preferably over the entire length of the human NT-proANP, respectively (in particular over the entire length). The degree of identity between two amino acid sequences can be determined by algorithms well known in the art and described elsewhere herein. Variants referred to above may be allelic variants or any other species specific homologs, paralogs, or orthologs. Moreover, the variants referred to herein include fragments or subunits of the specific NT-proANP polypeptide or the aforementioned types of variants as long as these fragments have the essential immunological and biological properties as referred to above. Such fragments may be, e.g., degradation products of the NT-proANP polypeptide. Further included are variants which differ due to posttranslational modifications such as phosphorylation or myristylation.

Determining the amount of a peptide or polypeptide referred to in this specification relates to measuring the amount or concentration semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal— may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay and methods which may utilize labelled molecules in various sandwich, competition, or other assay formats. Such assays are, preferably, based on detection agents such as antibodies which specifically recognize the peptide or polypeptide to be determined. The detection agents shall be either directly or indirectly capable of generating a signal indicating the presence or absence of the peptide or polypeptide. Moreover, the signal strength can, in certain embodiments, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, biosensors, optical devices coupled to immunoassays, biochips, analytical devices such as mass-spectrometers, NMR-analyzers, or chromatography devices. Further, methods include micro-plate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

In some embodiments, determining the amount of a peptide or polypeptide comprises the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide or polypeptide.

In other embodiments, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprises the steps of (a) contacting the peptide with a specific ligand, (b) (optionally) removing non-bound ligand, (c) measuring the amount of bound ligand.

According to some embodiments, said steps of contacting, removing and measuring may be performed by an analyzer unit of the system disclosed herein. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The bound ligand, in particular the ligand or the ligand/peptide complex, will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and $F(ab)_2$ fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Further suitable techniques for the determination of a polypeptide or peptide are described in the following.

First, binding of a ligand may be measured directly, e.g. by NMR or surface plasmon resonance. Measurement of the binding of a ligand, according to preferred embodiments, is performed by an analyzer unit of a system disclosed herein. Thereafter, an amount of the measured binding may be calculated by a computing device of a system disclosed herein. Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labelled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g. detectable) amount of product can be measured. Third, the ligand may be coupled covalently or non-covalently to a label allowing detection and measurement of the ligand. Labelling may be done by direct or indirect methods. Direct labelling involves coupling of the label directly (covalently or non-covalently) to the ligand. Indirect labelling involves binding (covalently or noncovalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a colored reaction product, fluorescence or chemoluminescence, which can be measured according to methods known in the art (e.g. using a light-sensitive film or a suitable camera system). As for measuring the enyzmatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}S$, $^{125}I$, $^{32}P$, $^{33}P$ and the like. A radioactive label can be detected by any method known and appropriate, e.g. a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS poly-acrylamid gel electrophoresis (SDS-PAGE), Western Blotting, and mass spectrometry), can be used alone or in combination with labelling or other detection methods as described above.

The amount of a peptide or polypeptide may be, also preferably, determined as follows: (a) contacting a solid support comprising a ligand for the peptide or polypeptide as specified above with a sample comprising the peptide or polypeptide and (b) measuring the amount peptide or polypeptide which is bound to the support. The ligand, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a microbead or microsphere, is present in suspension. The array consists of different microbeads or microspheres, possibly labelled, carrying different ligands. Methods of producing such arrays, for example based on solid-phase chemistry and photo-labile protective groups, are generally known (U.S. Pat. No. 5,744,305).

The term "amount" as used herein encompasses the absolute amount of a polypeptide or peptide, the relative amount or concentration of the said polypeptide or peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations. According to preferred embodiments of the subject invention, the determination of an "amount" is performed by the disclosed system, whereby a computing device determines the "amount" based on contacting and measuring steps performed by one or more analyzer units of said system.

In some embodiments, the amount of the polypeptides as referred to herein and, thus, of NT-proANP and NT-proBNP, are determined with the assays as described in the Examples section. For example, the amount of NT-proANP can be determined by detecting amino acids 1 to 98 of the pre-proANP peptide.

The term "comparing" as used herein encompasses comparing the amount of the peptide or polypeptide comprised by the sample to be analyzed with an amount of a suitable reference source specified elsewhere in this description. It is to be understood that comparing as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison referred to in step (b) of the method of the present invention may be carried out manually or computer assisted, e.g. by a computing device (e.g., of a system disclosed herein). For a computer assisted comparison, the value of the determined amount may be compared to values corresponding to suitable references which are stored in a database by a computer program. The computer program may further evaluate the result of the comparison, i.e. automatically provides the desired assessment in a suitable output format, i.e. the diagnostic result. The said diagnostic result may, preferably, serve as an aid for establishing the final clinical diagnosis by, e.g., a medical practitioner.

Based on the comparison of the determined and the reference amount, it is possible to assess whether the test subject has exhibited a TIA or not. For example, a result of a comparison may be given as raw data (absolute or relative amounts), and in some cases as an indicator in the form of a word, phrase, symbol, or numerical value which may be indicative of a particular diagnosis. Therefore, the reference amount is to be chosen so that either a difference or an identity in the compared amounts allows identifying those test subjects which belong into the group of subjects which are either have exhibited a TIA, or not. The method allows either excluding (rule-out) or identifying (rule-in) a subject who has exhibited a TIA, or not. Differences in the amounts, i.e. increases or decreases, as used herein, preferably, are differences which are statistically significant. Whether a difference is statistically significant can be determined by the statistical techniques referred to elsewhere herein. Similarly, an identity in the amounts encompasses identical amounts and those differences in the amounts which are not statistically significant and which are within the standard deviations for a measured parameter.

The term "reference amount" as used herein refers to an amount which allows for allocation of a subject into either (i) the group of subjects who have exhibited a TIA or (ii) the group of subjects who have not exhibited a TIA. Said rule-in and/or rule-out diagnosis may be provided by the computing device of a system disclosed herein based on said comparison of the calculated "amount" to a reference or a threshold. For example, a computing device of a system may provide an indicator, in the form of a word, symbol, or numerical value which is indicative of one of a rule-in or rule-out diagnosis. The reference amount applicable for an individual subject may vary depending on various physiological parameters such as age, gender, or subpopulation, as well as on the means used for the determination of the polypeptide or peptide referred to herein. A suitable reference amount may be determined from a reference sample to be analyzed together, i.e. simultaneously or subsequently, with the test sample.

Reference amounts can, in principle, be calculated for a cohort of subjects as specified above based on the average or mean values for a given biomarker by applying standard methods of statistics. In particular, accuracy of a test such as a method aiming to diagnose an event, or not, is best described by its receiver-operating characteristics (ROC) (see especially Zweig 1993, Clin. Chem. 39:561-577). The ROC graph is a plot of all of the sensitivity versus specificity pairs resulting from continuously varying the decision threshold over the entire range of data observed. The clinical performance of a diagnostic method depends on its accuracy, i.e. its ability to correctly allocate subjects to a certain prognosis or diagnosis. The ROC plot indicates the overlap between the two distributions by plotting the sensitivity versus 1-specificity for the complete range of thresholds suitable for making a distinction. On the y-axis is sensitivity, or the true-positive fraction, which is defined as the ratio of number of true-positive test results to the product of number of true-positive and number of false-negative test results. This has also been referred to as positivity in the presence of a disease or condition. It is calculated solely from the affected subgroup. On the x-axis is the false-positive fraction, or 1-specificity, which is defined as the ratio of number of false-positive results to the product of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity/specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. Dependent on a desired confidence interval, a threshold can be derived from the ROC curve allowing for the diagnosis or prediction for a given event with a proper balance of sensitivity and specificity, respectively. Accordingly, the reference to be used for the aforementioned method of the present invention, i.e. a threshold which allows to discriminate between subjects who have exhibited a TIA or those who have not exhibited a TIA can be generated, preferably, by establishing a ROC for said cohort as described above and deriving a threshold amount therefrom. Dependent on a desired sensitivity and specificity for a diagnostic method, the ROC plot allows deriving suitable thresholds. It will be understood that an optimal sensitivity is desired for excluding TIA (i.e. a rule out) whereas an optimal specificity is envisaged for a subject to be assessed to have exhibited a TIA (i.e. a rule in). Moreover, it is preferred that the amounts determined in step a) of the method of the present invention are compared to more than one reference amounts, e.g. a reference amount for ruling in TIA and a reference amount for ruling out TIA.

The reference amount(s) is (are) derived from a sample from a subject (or group of subjects) known to have exhibited a TIA (in particular within the window periods as specified elsewhere herein), and/or from a sample from a subject (or group of subjects) known not to have exhibited a TIA (in particular within the window periods as specified elsewhere herein).

The subject known not to have exhibited a TIA is, preferably, a healthy subject. Also the subject known not to have exhibited a TIA did not exhibit a stroke, in particular within the window periods as referred to above.

It is also preferred that the reference subject (i.e. the subject known to have exhibited a TIA or subject known not to have exhibited a TIA) has risk factors for an acute cerebral ischemic event, in particular for TIA. Preferred risk factors for an acute cerebral ischemic event, in particular for TIA include coronary artery disease, heart failure, in particular heart failure, systolic and/or diastolic cardiac dysfunction, valvular heart disease, and arterial hypertension. Further risk factors are diabetes and obesity. Accordingly, the reference subject preferably, shows at least one of these risk factors. Preferably, the reference subject suffers from coronary artery disease. Even more preferably, the reference subject suffers from heart failure. Most preferably, the reference subject as well as the test subject suffers from heart failure. Also preferably, the reference subject as well as the test subject suffers from heart failure. This applies in particular, if the amounts of NT-proANP and NT-proBNP are determined and if the ratio of the amounts of NT-proANP to NT-proBNP is calculated in the context of the method of the present invention (see elsewhere herein).

If only the amount of NT-proANP is determined, it is also preferred that neither the reference subject nor the test subject suffers from heart failure or coronary artery disease.

The following applies as diagnostic algorithms.

In certain embodiments, the reference amount is
a. derived from a sample from a subject (or group of subjects) known to have exhibited a TIA, wherein an amount of NT-proANP in the sample from the test subject which is essentially identical to the reference amount or which is larger than the reference amount indicates that the subject has exhibited a transitory ischemic attack, and/or
b. derived from a sample from a subject known not have exhibited a TIA, wherein an amount of NT-proANP in the sample from the test subject which is essentially identical to the reference amount or which is lower than the reference amount indicates that the subject has not exhibited a transitory ischemic attack.

A reference amount derived from a sample from a subject (or group of subjects) known to have exhibited a TIA is about 54500 pg/ml to about 150000 pg/ml and, more particularly, about 54500 to about 137800 pg/ml. Even more particularly, a reference amount derived from a sample from a subject (or group of subjects) known to have exhibited a TIA is about 137500, or 94800, or, most particularly, 54500 pg/ml.

A reference amount derived from a sample from a subject (or group of subjects) known to not have exhibited a TIA is about 1000 pg/ml to about 33600 pg/ml and, more particularly, about 1000 to about 12570 pg/ml. Even more particularly, a reference amount derived from a sample from a subject (or group of subjects) known not to have exhibited a TIA is about 33600, or 15000, or, most particularly 12570 pg/ml. In some embodiments, the reference amount is 4662 pg/ml.

Further, the reference amount may define a threshold amount, in particular a calculated reference amount, whereby an amount NT-proANP in the sample of the test subject larger than the respective threshold shall be indicative for a TIA, while an amount of NT-proANP in the sample of the test subject lower than the calculated reference amount shall indicate that the subject did not exhibit a TIA. A particular threshold amount being a calculated reference amount is about 54500 pg/ml, or more preferably, 45000 pg/ml.

The term "about" as used herein means+/−20%, +/−10%, +/−5%, +−2% or +−/1% from the specific values referred to.

In a preferred embodiment of the method of the present invention, a TIA shall be ruled in. In this case, the reference amount is derived from a sample of subject (or samples from a group of subjects) known to have exhibited a TIA.

Accordingly, the present invention envisages a method for ruling in a transitory ischemic attack (TIA) in a subject who is suspected to have exhibited a transitory ischemic attack, but who did not exhibit a stroke, said method comprising the steps of
 a. determining the amount of NT-proANP in a sample from said subject, and
 b. comparing the determined amount of NT-proANP to a reference amount, whereby a transitory ischemic attack is ruled in,
wherein the reference amount is derived from a sample from a subject (or from samples of group of subjects) known to have exhibited a TIA, wherein an amount of NT-proANP in the sample from the test subject which is essentially identical to the reference amount or which is larger than the reference amount indicates that the subject has exhibited a transitory ischemic attack.

In a preferred embodiment of the method of the present invention, a TIA shall be ruled in. In this case, the reference amount is derived from a sample of subject (or samples from a group of subjects) known not to have exhibited a TIA.

Accordingly, the present invention envisages a method for ruling out a transitory ischemic attack (TIA) in a subject who is suspected to have exhibited a transitory ischemic attack, but who did not exhibit a stroke, said method comprising the steps of
 a. determining the amount of NT-proANP in a sample from said subject, and
 b. comparing the, thus, determined amount of NT-proANP to a reference amount, whereby a transitory ischemic attack is ruled out,
wherein the reference amount is derived from a sample from a subject (or from samples of group of subjects) known to have exhibited a TIA, wherein an amount of NT-proANP in the sample from the test subject which is essentially identical to the reference amount or which is lower than the reference amount indicates that the subject has not exhibited a transitory ischemic attack.

In a further preferred embodiment of the present invention, the aforementioned method further comprises the steps of determining the amount of NT-proBNP in a sample from the subject, and calculating the ratio of the amount of NT-proANP and the amount of NT-proBNP. The determination of both markers is advantageous, since the ratio of the amounts of both markers allows for a particularly reliable diagnosis of TIA in subject with heart failure (see Examples).

According, the present invention, in particular, is directed to a method for diagnosing a transitory ischemic attack (TIA) in a subject who is suspected to have exhibited a transitory ischemic attack, but who did not exhibit a stroke, comprising
 a. determining the amount of NT-proANP in a sample from said subject,
 b. determining the amount of NT-proBNP in a sample from said subject, and c. calculating of a ratio of the amounts of NT-proANP and NT-proBNP.

In some embodiments, the amounts determined in a) and b) above are determined in the same sample. However, it is also envisaged to determine the amounts in different samples.

In certain embodiments, the method further comprises the comparison of the calculated ratio to a reference ratio, thereby diagnosing TIA in said subject.

Thus, the present invention also relates to a method for diagnosing a transitory ischemic attack (TIA) in a subject who is suspected to have exhibited a transitory ischemic attack, but who did not exhibit a stroke, comprising
  a. determining the amount of NT-proANP in a sample from said subject,
  b. determining the amount of NT-proBNP in a sample from said subject,
  c. calculating of a ratio of the amounts of NT-proANP and NT-proBNP, and
  d. comparing the calculated ratio to a reference ratio, thereby diagnosing TIA in said subject.

The marker NT-proBNP (N-terminal pro-brain natriuretic peptide) is well known in the art. NT-proBNP is a polypeptide comprising, preferably, 76 amino acids in length corresponding to the N-terminal portion of the human brain natriuretic peptide (BNP) molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NT-proBNP referred to in accordance with the present invention further encompasses allelic and other variants of said specific sequence for human NT-proBNP discussed above. Specifically, envisaged are variant polypeptides which are on the amino acid level at least 60% identical, more preferably at least 70%, at least 80%, at least 90%, at least 95%, at least 98% or at least 99% identical, to human NT-proBNP, preferably, over the entire length. The degree of identity between two amino acid sequences, in principle, can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith 1981, Add. APL. Math. 2:482, by the homology alignment algorithm of Needleman 1970, J. Mol. Biol. 48:443, by the search for similarity method of Pearson 1988, Proc. Natl. Acad Sci. (USA) 85: 2444, by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are immunological and/or biological properties. Preferably, the NT-proBNP variants have immunological properties (i.e. epitope composition) comparable to those of NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Invest 59:177-181), Yeo et al. (Yeo 2003, Clinica Chimica Acta 338:107-115). Variants also include posttranslationally modified peptides such as glycosylated or myristylated peptides. Further, a variant in accordance with the present invention is also a peptide or polypeptide which has been modified after collection of the sample, for example by covalent or non-covalent attachment of a label, particularly a radioactive or fluorescent label, to the peptide.

The term "calculating" as used herein refers to assessing the ratio of the amount of NT-proANP and NT-proBNP determined in the sample(s) of the subject. In accordance with the present invention the ratio of the amount of NT-proANP to the amount of NT-proBNP, or the ratio of the amount of NT-proBNP to the amount of NT-proANP can be determined Preferably, the ratio of the amount of NT-proANP to the amount of NT-proBNP is determined.

Preferred reference subjects are disclosed herein above. Preferably, the reference ratio is derived from a sample from a subject (or from samples group of subjects) known to have exhibited a TIA, and/or from a sample from a subject (or from samples group of subjects) known not to have exhibited a TIA (see also explanations made herein above).

The following applies as diagnostic algorithms, if the calculated ratio (and the reference ratio) is ratio of the amount of NT-proANP to the amount of NT-proBNP:
  In certain embodiments, the reference ratio is
  a. derived from a sample from a subject (or from samples group of subjects) known to have exhibited a TIA, wherein a ratio in the sample from the test subject which is essentially identical to the reference ratio or which is larger than the reference ratio indicates that the subject has exhibited a transitory ischemic attack, and/or
  b. derived from a sample from a subject (or from samples group of subjects) known not have exhibited a TIA, wherein ratio in the sample from the test subject which is essentially identical to the reference ratio or which is lower than the reference ratio indicates that the subject has not exhibited a transitory ischemic attack.

The following applies as diagnostic algorithms, if the calculated ratio (and the reference ratio) is the ratio of the amount of NT-proBNP to the amount of NT-proANP.
  In some embodiments, the reference ratio is
  a. derived from a sample from a subject (or from samples group of subjects) known to have exhibited a TIA, wherein a ratio in the sample from the test subject which is essentially identical to the reference ratio or which is lower than the reference ratio indicates that the subject has exhibited a transitory ischemic attack, and/or b. derived from a sample from a subject (or from samples group of subjects) known not have exhibited a TIA, wherein ratio in the sample from the test subject which is essentially identical to the reference ratio or which is larger than the reference ratio indicates that the subject has not exhibited a transitory ischemic attack.

Further, the reference ratio may define a threshold ratio, in particular a calculated reference ratio, whereby a ratio of the amount of NT-proANP to NT-proBNP in the sample of the test subject larger than the respective threshold shall be indicative for a TIA, while a ratio of the amount of NT-proANP to NT-proBNP in the sample of the test subject lower than the respective threshold shall indicate that the subject did not exhibit a TIA (if the ratio of the amount of NT-proANP to NT-proBNP is determined).

A reference ratio for the amount of NT-proANP to the amount of NT-proBNP derived from a sample from a subject (or group of subjects) known to not have exhibited a TIA is about 10 to about 125 and, more particularly, about 20 to about 100, or about 20 to about 90. Even more particularly, a reference ratio derived from a sample from a subject (or group of subjects) known not to have exhibited a TIA is about 125, or, most particularly, about 80.

If the reference ratio is derived from a subject who has risk factors for TIA (as described elsewhere herein, in particular from a subject who suffers from heart failure), a reference ratio for the amount of NT-proANP to the amount of NT-proBNP derived from a sample from a subject (or group of subjects) known to not have exhibited a TIA is about 10 to about 40 and, more particularly, about 20 to about 40, or about 20 to about 30. Even more particularly, a reference ratio derived from a sample from a subject (or group of subjects) known not to have exhibited a TIA is about 40, or, most particularly, about 30.

A reference ratio for the amount of NT-proANP to the amount of NT-proBNP derived from a sample from a subject (or group of subjects) known to have exhibited a TIA is about 150 to about 300 and, more particularly, about 150 to about 250, or about 200 to about 250. Even more particularly, a reference ratio derived from a sample from a subject (or group of subjects) known to have exhibited a TIA is about 250, or, most particularly, about 200.

In an embodiment of the present invention, the method further comprises the step of recommending a suitable therapy if a TIA has been diagnosed.

The term "recommending" as used herein means establishing a proposal for a therapy which could be applied to the subject. However, it is to be understood that applying the actual therapy whatsoever is not comprised by the term. The therapy to be recommended depends on the outcome of the diagnosis provided by the method of the present invention. The recommendation step referred to above can also, preferably, be automated. Preferably, the diagnosis or aid for diagnosis obtained from the step b) of the method of the present invention, i.e. the diagnostic result of the method, will be used to search a database comprising recommendations of therapeutic measures for the individual possible diagnostic results. Suitable therapies that can be recommended in case TIA has been diagnosed are well known in the art and, preferably, encompass those treatment regimen which aim to reduce the risk of further cerebral ischemic events, in particular the risk of stroke and/or TIA. These treatments include administration of pharmaceuticals, interventions as well as lifestyle changes. The treatment may depend on the cause of TIA. Preferred treatment regimen include anticoagulation therapy, anti platelet therapy, intake of aspirin and/or heparin, stenting (see Chimowitz et al. NEJM 2011: 993-1003), and endarterectomy, in particular carotid endarterectomy. Preferred lifestyle changes are abstention from smoking and/or alcohol, and weight loss (in particular by reduced calorie intake and/or by increased physical exercise).

In an aspect of the invention, a method for establishing an aid for diagnosing a transitory ischemic attack (TIA) in a subject who is suspected to have exhibited a transitory ischemic attack, but who did not exhibit a stroke, is contemplated, said method comprising:
a) determining the amount of the marker NT-proANP by (i) bringing the sample into contact with a detection agent that specifically binds to said marker for a time sufficient to allow for the formation of a complex of the said detection agent and the marker from the sample, (ii) measuring the amount of the formed complex, wherein the said amount of the formed complex is proportional to the amount of the marker present in the sample, and (iii) transforming the amount of the formed complex into an amount of the marker reflecting the amount of the marker present in the sample;
b) comparing said amount to a reference; and
c) establishing an aid for diagnosing a transitory ischemic attack (TIA) based on the result of the comparison made in step b).

In another aspect of the invention, a system for diagnosing a transitory ischemic attack (TIA) in a subject who is suspected to have exhibited a transitory ischemic attack, but who did not exhibit a stroke, is contemplated, comprising:
a) an analyzer unit configured to bringing the sample into contact with a detection agent that specifically binds to the marker NT-proANP for a time sufficient to allow for the formation of a complex of the said detection agent and the marker from the sample,
b) an analyzer unit configured to measure the amount of the formed complex, wherein the said amount of the formed complex is proportional to the amount of the marker present in the sample,
c) a computing device having a processor and in operable communication with said analysis units, and
d) a non-transient machine readable media including a plurality of instructions executable by the processor, the instructions, when executed transform the amount of the formed complex into an amount of the marker reflecting the amount of the marker present in the sample, compare said amount to a reference, and establish an aid for diagnosing a transitory ischemic attack (TIA) on the result of said comparison to said reference.

A suitable detection agent may be, in an aspect, an antibody which specifically binds to the marker in a sample of a subject to be investigated by the method of the invention. Another detection agent that can be applied, in an aspect, may be an aptamer which specifically binds to the marker in the sample. In yet an aspect the sample is removed from the complex formed between the detection agent and the marker prior to the measurement of the amount of formed complex. Accordingly, in an aspect, the detection agent may be immobilized on a solid support. In yet another aspect, the sample can be removed from the formed complex on the solid support by applying a washing solution. The formed complex shall be proportional to the amount of the marker present in the sample. It will be understood that the specificity and/or sensitivity of the detection agent to be applied defines the degree of proportion of at least one marker comprised in the sample which is capable of being specifically bound. Further details on how the determination can be carried out are also found elsewhere herein. The amount of formed complex shall be transformed into an amount of at least one marker reflecting the amount indeed present in the sample. Such an amount, in an aspect, may be essentially the amount present in the sample or may be, in another aspect, an amount which is a certain proportion thereof due to the relationship between the formed complex and the amount present in the original sample.

In yet an aspect of the aforementioned method, step a) may be carried out by an analyzer unit, in an aspect, an analyzer unit as defined elsewhere herein.

In an aspect of the method of the invention, the amount determined in step a) is compared to a reference. In an aspect, the reference is a reference as defined elsewhere herein. In yet another aspect, the reference takes into account the proportional relationship between the measured amount of complex and the amount present in the original sample. Thus, the references applied in an aspect of the method of the invention are artificial references which are adopted to reflect the limitations of the detection agent that has been used. In another aspect, said relationship can be also taken into account when carrying out the comparison, e.g., by including a normalization and/or correction calculation step for the determined amount prior to actually comparing the value of the determined amount and the reference. Again, the normalization and/or correction calculation step for the determined amount adopts the comparison step such that the limitations of the detection agent that has been used are reflected properly. In an aspect, the comparison is carried out automatically, e.g., assisted by a computer system or the like.

The aid for diagnosing TIA is established based on the comparison carried out in step b) by allocating the subject either into a group of subjects having exhibited a TIA, or not having exhibited a TIA as set forth herein elsewhere. As discussed elsewhere herein already, the allocation of the investigated subject may not be correct in 100% of the investigated cases. Moreover, the groups of subjects into which the investigated subject is allocated are artificial groups in that they are established based on statistical considerations, i.e. a certain preselected degree of likelihood based on which method of the invention shall operate. In an aspect of the invention, the aid for diagnosing TIA is established automatically, e.g., assisted by a computing device or the like, as described and disclosed herein.

In an aspect of the method of the invention, said method further comprises a step of recommending and/or managing the subject according to the result established in step c) as set forth elsewhere herein in detail, and/or adapting intensiveness of disease monitoring.

In an aspect of the aforementioned method, steps b) and/or c) are carried out by one or more analyzer units as set forth elsewhere herein.

The explanations and definitions given herein above apply mutatis mutandis to the following.

Method for Diagnosing an Acute Cerebral Ischemic Event

The inventors have further shown that the ratio of the amount of NT-proANP and the amount of NT-proBNP is a valuable indicator for the diagnosis of acute cerebral ischemic events in a subject.

The present invention, therefore, further relates to a method for diagnosing an acute cerebral ischemic event in a subject who is suspected to suffer from an acute cerebral ischemic event, comprising a. determining the amount of NT-proANP in a sample from said subject,
b. determining the amount of NT-proBNP in a sample from said subject, and
c. calculating of a ratio of the amounts of NT-proANP and NT-proBNP.

In a preferred embodiment, the aforementioned method further comprises the comparison of the calculated ratio to a reference ratio, thereby diagnosing the acute cerebral ischemic event.

Accordingly, the present invention, in particular, relates to a method for diagnosing an acute cerebral ischemic event in a subject who is suspected to suffer from an acute cerebral ischemic event, comprising a. determining the amount of NT-proANP in a sample from said subject,
b. determining the amount of NT-proBNP in a sample from said subject,
c. calculating of a ratio of the amounts of NT-proANP and NT-proBNP, and
d. comparing the calculated ratio to a reference ratio, thereby diagnosing the acute cerebral ischemic event.

The term "acute cerebral ischemic event" is well understood by the skilled person. The term, in particular, relates to an acute condition in which the blood flow to the brain (or the parts of the brain) is insufficient to the metabolic demand of the brain. There are two types of acute cerebral ischemic events: 1. the ischemia associated with the event may be confined to a specific region of the brain (focal ischemia); or 2. the ischemia associated with the event may encompass wide areas of brain tissue (systemic ischemia). The event is acute, and, thus appears suddenly. For the description herein, the acute cerebral ischemic event is selected from stroke and a transitory ischemic attack. The terms "stroke" and "transitory ischemic attack" are defined elsewhere herein.

The term "subject" has been described elsewhere herein as used herein relates to animals, preferably mammals, and, more preferably, humans. The subject according to the present invention shall be suspected to have exhibited an acute cerebral ischemic event. In some embodiments, said subject shall be suspected to have exhibited an acute cerebral ischemic event within 72 hours, in other embodiments within 48 hours, and in other embodiments within 24 hours before the sample to be tested has been obtained. Accordingly, another aspect of the present invention is diagnosis of whether the test subject has exhibited an acute cerebral ischemic event, or has not exhibited an acute cerebral ischemic event, preferably, within 72 hours, more preferably, within 48 hours, and, most preferably, within 24 hours before the sample to be tested has been obtained.

In some embodiments, the test subject (and/or the reference subject) has risk factors for an acute cerebral ischemic event. Such risk factors include coronary artery disease, heart failure, in particular acute heart failure, systolic and/or diastolic cardiac dysfunction, valvular heart disease, and arterial hypertension. Further risk factors are diabetes and obesity. Accordingly in such embodiments, the test subject shows at least one of these risk factors. In particular, it is envisaged that the test subject (and/or the reference subject, i.e. the subject from which the reference amount is derived from) suffers from coronary artery disease and/or from heart failure. In some embodiments, the subject suffers from heart failure. The same applies to the reference subject.

As set forth above, the subject to be tested in accordance with the aforementioned method shall be suspected to suffer from an acute cerebral ischemic event, and, thus, to have exhibited an acute cerebral ischemic event within certain window periods as set forth elsewhere herein. Preferably, a subject who is suspected to have exhibited an acute cerebral ischemic event is a subject who has shown symptoms of an acute cerebral ischemic event. Said subject is a subject who has shown symptoms of an acute cerebral ischemic event within a certain window period prior to obtaining the test sample. In certain embodiments, said subject has shown symptoms of acute cerebral ischemic event within 72 hours, in other embodiments within 48 hours, and in other embodiments within 24 hours before the sample has been obtained. Preferably, however, the test sample shall be obtained later than 1 hour, in particular, later than 2 hours after the onset of symptoms of acute cerebral ischemic event.

By the aforementioned method of the present invention, an acute cerebral ischemic event shall be diagnosed. The term "diagnosing" as used herein means assessing whether a subject as referred to in accordance with the method of the present invention has exhibited an acute cerebral ischemic event, or not. In particular, it shall be diagnosed whether the subject has exhibited an acute cerebral ischemic event, or not within a certain window period before obtaining the sample to be tested. In a preferred embodiment, it shall be diagnosed whether the subject has exhibited an acute cerebral ischemic event, or not, within 72 hours before obtaining the sample to be tested. In a further preferred embodiment, it shall be diagnosed whether the subject has exhibited an acute cerebral ischemic event, or not, within 48 hours before obtaining the sample to be tested. In an even further preferred embodiment, it shall be diagnosed whether the subject has exhibited an acute cerebral ischemic event, or not, within 24 hours before obtaining the sample to be tested. Preferably, the subject does not show symptoms of the acute cerebral ischemic event anymore at the time at which the sample is obtained.

In some embodiments, said sample is obtained not more than 72 hours after the onset of symptoms of an acute cerebral ischemic event. In other embodiments, said sample is obtained not more than 48 hours, and, in others, not more than 24 hours after the onset of symptoms of an acute cerebral ischemic event. Preferably, the subject does not show symptoms of an acute cerebral ischemic event anymore at the time at which the sample is obtained.

In certain embodiments, the reference ratio is derived from a sample from a subject (or from samples group of subjects) known to have exhibited an acute cerebral ischemic event, and/or from a sample from a subject (or from samples group of subjects) known not to have exhibited an acute cerebral ischemic event.

It is preferred that the reference subject (i.e. the subject known to have exhibited an acute cerebral ischemic event or subject known not to have exhibited an acute cerebral ischemic event) has risk factors for an acute cerebral ischemic event. Such risk factors for an acute cerebral ischemic event are disclosed herein above and include coronary artery disease, heart failure, in particular heart failure, systolic and/or diastolic cardiac dysfunction, valvular heart disease, and arterial hypertension. Further risk factors are diabetes and obesity. Accordingly, the reference subject generally shows at least one of these risk factors.

The following applies as diagnostic algorithms, if the calculated ratio (and the reference ratio) is ratio of the amount of NT-proANP to the amount of NT-proBNP:

In some embodiments, the reference ratio is derived from a sample from a subject known to have exhibited an acute cerebral ischemic event, wherein a ratio of NT-proANP to NT-proBNP in the sample from the test subject which is essentially identical to the reference ratio or which is larger than the reference ratio indicates that the subject has exhibited an acute cerebral ischemic event, and/or the reference ratio is derived from a sample from a subject known not to have exhibited an acute cerebral ischemic event, and wherein a ratio of NT-proANP to NT-proBNP in the sample from the test subject which is essentially identical to the reference ratio or which is lower than the reference ratio indicates that the subject has not exhibited an acute cerebral ischemic event.

A reference ratio range for the amount of NT-proANP to the amount of NT-proBNP derived from a sample from a subject (or group of subjects) known to not have exhibited an acute cerebral ischemic event is about 10 to about 100 and, more preferably, about 20 to about 90, or about 20 to about 80. Even more preferably, a reference ratio is derived from a sample from a subject (or group of subjects) known not to have exhibited an acute cerebral ischemic event is about 100, or, most preferably, about 80.

If the reference ratio is derived from a subject who has risk factors for an acute cerebral ischemic event, in particular from a subject suffering from heart failure or coronary artery disease, a reference ratio range for the amount of NT-proANP to the amount of NT-proBNP derived from a sample from a subject (or group of subjects) known to not have exhibited an acute cerebral ischemic event is about 10 to about 40 and, more preferably, about 20 to about 40, or about 20 to about 30. Even more preferably, a reference derived from a sample from a subject (or group of subjects) known not to have exhibited an acute cerebral ischemic event is about 40, or, most preferably, about 30.

A reference ratio range for the amount of NT-proANP to the amount of NT-proBNP derived from a sample from a subject (or group of subjects) known to have exhibited a acute cerebral ischemic event is about 100 to about 250 and, more preferably, about 100 to about 200, or about 100 to about 150. Even more preferably, a reference derived from a sample from a subject (or group of subjects) known to have exhibited a acute cerebral ischemic event is about 100, or, most preferably, about 150. Preferred reference amount for TIA are disclosed elsewhere herein.

In an aspect of the invention, a method for establishing an aid for diagnosing an acute cerebral ischemic event in a subject who is suspected to suffer from an acute cerebral ischemic event, is contemplated, said method comprising:
a) determining the amount of the markers NT-proANP and NT-proBNP by (i) bringing the sample into contact with detection agents that specifically bind to said markers for a time sufficient to allow for the formation of a complex of the said detection agent and the marker from the sample, (ii) measuring the amount of the formed complex, wherein the said amount of the formed complex is proportional to the amount of the marker present in the sample, and (iii) transforming the amount of the formed complex into an amount of the marker reflecting the amount of the markers present in the sample;
b) calculating of a ratio of the amounts of NT-proANP and NT-proBNP.
c) comparing said ratio to a reference ratio; and
c) establishing an aid for diagnosing an acute cerebral ischemic event based on the result of the comparison made in step c).

In another aspect of the invention, a system for diagnosing an acute cerebral ischemic event in a subject who is suspected to suffer from an acute cerebral ischemic event, is contemplated, comprising:
a) an analyzer unit configured to bring the sample into contact with a detection agent that specifically binds to the marker NT-proANP for a time sufficient to allow for the formation of a complex of the said detection agent and the marker from the sample, b) an analyzer unit configured to measure the amount of the formed complex, wherein the said amount of the formed complex is proportional to the amount of the marker present in the sample, c) a computing device having a processor and in operable communication with said analysis units, and d) a non-transient machine readable media including a plurality of instructions executable by the processor, the instructions, when executed transform the amount of the formed complex into an amount of the marker reflecting the amount of the marker present in the sample, compare said amount to a reference, and establish an aid for diagnosing an acute cerebral ischemic event based on the result of said comparison to said reference.

A suitable detection agent may be, in an aspect, an antibody which is specifically binds to the marker in a sample of a subject to be investigated by the method of the invention as set forth elsewhere herein.

In yet an aspect of the aforementioned method, step a) may be carried out by an analyzer unit, in an aspect, an analyzer unit as defined elsewhere herein.

In an aspect of the method of the invention, the ratio calculated in step b) is compared to a reference ratio. In an aspect, the reference ratio is a reference as defined elsewhere herein. Thus, the references applied in an aspect of the method of the invention may be artificial references which are adopted to reflect the limitations of the detection agent that has been used. In another aspect, said relationship can be also taken into account when carrying out the comparison, e.g., by including a normalization and/or correction calculation step for the determined amount or ratio prior to actually comparing the value of the determined amount and the reference. In an aspect, the comparison is carried out automatically, e.g., assisted by a computer system or the like.

The aid for diagnosing an acute cerebral ischemic event is established based on the comparison carried out in step c) by allocating the subject either into a group of subjects suffering from an acute cerebral event, or not suffering from an acute cerebral event as set forth herein elsewhere. As discussed elsewhere herein already, the allocation of the investigated subject may not be correct in 100% of the investigated cases. Moreover, the groups of subjects into which the investigated subject is allocated may include artificial groups in that they are established based on statistical considerations, i.e. a certain preselected degree of likelihood based on which the method of the invention shall operate. In an aspect of the invention, the aid for diagnosing an acute cerebral event is established automatically, e.g., assisted by a computing device or the like, as described and disclosed herein.

In an aspect of the method of the invention, said method further comprises a step of recommending and/or managing the subject according to the result established in step c) as set forth elsewhere herein in detail, and/or adapting intensiveness of disease monitoring.

In an aspect of the aforementioned method, steps b) and/or c) are carried out by one or more analyzer units as set forth elsewhere herein.

Furthermore, the present invention relates to the use of the NT-proANP polypeptide and/or of a detection agent, which specifically binds thereto in a sample of a subject who is suspected to have exhibited a transitory ischemic attack (TIA) for diagnosing a transitory ischemic attack.

Further, the present invention relates to the use of the NT-proANP polypeptide and of the NT-proBNP polypeptide in a sample of a subject who is suspected to have exhibited a transitory ischemic attack (TIA) for diagnosing a transitory ischemic attack.

Also, the present invention relates to the use of a detection agent which specifically binds to the NT-proANP polypeptide and of a detection agent, which specifically binds to the NT-proBNP polypeptide in a sample of a subject who is suspected to have exhibited a transitory ischemic attack (TIA) for diagnosing a transitory ischemic attack.

Moreover, the present invention relates to the use of the NT-proANP polypeptide and of the NT-proBNP polypeptide in a sample of a subject who is suspected suffer from an acute cerebral ischemic event for diagnosing an acute cerebral ischemic event.

Further, the present invention relates to the use of a detection agent which specifically binds to the NT-proANP polypeptide and of a detection agent, which specifically binds to the NT-proBNP polypeptide in a sample of a subject who is suspected suffer from an acute cerebral ischemic event for diagnosing an acute cerebral ischemic event.

The term "detection agent" as used herein refers to an agent which is capable of specifically recognizing and binding the biomarker referred to herein (NT-proANP or NT-proBNP) when present in a sample. Moreover, said agent shall allow for direct or indirect detection of the complex formed by the said agent and the biomarker. Direct detection can be achieved by including into the agent a detectable label. Indirect labelling may be achieved by a further agent which specifically binds to the complex comprising the biomarker and the detection agent wherein the said further agent is than capable of generating a detectable signal. Suitable compounds which can be used as detection agents are well known in the art. Preferably, the detection agent is an antibody or aptamere which specifically binds to the biomarker. Antibodies as referred to herein include both polyclonal and monoclonal antibodies, as well as fragments thereof, such as Fv, Fab and F(ab)$_2$ fragments that are capable of binding antigen or hapten. Also envisaged are single chain antibodies and humanized hybrid antibodies wherein amino acid sequences of a non-human donor antibody exhibiting a desired antigen-specificity are combined with sequences of a human acceptor antibody.

The present invention further relates to a device for diagnosing a transitory ischemic attack, said device comprising:

a) an analyzing unit comprising a detection agent for the NT-proANP polypeptide which allows for the determination of the amount of said NT-proANP polypeptide; and b) an evaluation unit comprising a data processor having implemented an algorithm for comparing the amount determined by the analyzing unit with the reference amount stored in a database in order to establish the diagnosis of NT-proANP, wherein the reference amount is derived from a sample from a subject as described herein elsewhere in the context of the method for diagnosing a TIA, and the algorithm is an algorithm as set forth in the context of the said method.

According to a further aspect of the present invention, a device adapted for carrying out a method of the invention is provided comprising a) an analyzer unit comprising a detection agent for the NT-proANP polypeptide which allows for the determination of the amount of said NT-proANP polypeptide; and b) an analyzer unit for comparing the determined amount with a reference amount, whereby it is diagnosed whether the subject has exhibited a TIA, said unit comprising a database with a reference amount values and a computer-implemented algorithm carrying out the comparison.

The present invention further relates to a device for diagnosing a transitory ischemic attack, said device comprising:
  a) an analyzing unit comprising a detection agent for the NT-proANP polypeptide which allows for the determination of the amount of said NT-proANP polypeptide, and a detection agent for the NT-proBNP polypeptide which allows for the determination of the amount of said NT-proBNP polypeptide; and
  b) an evaluation unit comprising a data processor for calculating a ratio of the amounts of NT-proANP and NT-proBNP determined by the analyzing unit, said data processor having implemented an algorithm for comparing the ratio with the reference ratio stored in a database in order to establish the diagnosis of a TIA, wherein the reference ratio is derived from a sample from a subject as described herein elsewhere in the context of the method for diagnosing a TIA, and the algorithm is an algorithm as set forth in the context of the said method.

The present invention further relates to a device for diagnosing a acute cerebral ischemic event, said device comprising:
  a) an analyzing unit comprising a detection agent for the NT-proANP polypeptide which allows for the determination of the amount of said NT-proANP polypeptide, and a detection agent for the NT-proBNP polypeptide which allows for the determination of the amount of said NT-proBNP polypeptide; and
  b) an evaluation unit comprising a data processor for calculating a ratio of the amounts of NT-proANP and NT-proBNP determined by the analyzing unit, said data processor having implemented an algorithm for comparing the ratio with the reference ratio stored in a database in order to establish the diagnosis of a TIA, wherein the reference ratio is derived from a sample from a subject as described herein elsewhere in the context of the method for diagnosing an acute cerebral ischemic event, and the algorithm is an algorithm as set forth in the context of the said method.

Also contemplated is a device for diagnosing an acute cerebral ischemic event, said device comprising:
  a) an analyzer unit comprising a detection agent for the NT-proANP polypeptide which allows for the determination of the amount of said NT-proANP polypeptide, and a detection agent for the NT-proBNP polypeptide which allows for the determination of the amount of said NT-proBNP polypeptide; and
  b) an analyser unit comprising a data processor for calculating a ratio of the amounts of NT-proANP and NT-proBNP, said data processor having implemented an algorithm for comparing the ratio with the reference ratio stored in a database in order to establish the diagnosis of the event, wherein the reference ratio is derived from a sample from a subject as described herein elsewhere in the context of the method for diagnosing an acute cerebral ischemic event, and the algorithm is an algorithm as set forth in the context of the said method.

The term "device" as used herein relates to a system comprising the aforementioned units operatively linked to each other as to allow the diagnosis according to the methods of the invention. Preferred detection agents which can be used for the analyzing unit are disclosed elsewhere herein. The analyzing unit, preferably, comprises said detection agents in immobilized form on a solid support which is to be contacted to the sample comprising the biomarkers the amount of which is to be determined. Moreover, the analyzing unit can also comprise a detector which determines the amount of detection agent which is specifically bound to the biomarker(s). The determined amount can be transmitted to the evaluation unit. Said evaluation unit comprises a data processing element, such as a computer, with an implemented algorithm for carrying out a comparison between the determined amount and a suitable reference. Suitable references can be derived from samples of subjects to be used for the generation of reference amounts as described elsewhere herein above. The diagnostic results may be given as output of parametric diagnostic raw data, preferably, as absolute or relative amounts. It is to be understood that these data may need interpretation by the clinician. However, also envisaged are expert system devices wherein the output comprises processed diagnostic raw data the interpretation of which does not require a specialized clinician. Preferably, the device of the present invention can be used to carry out the aforementioned method of the present invention in an automated manner.

A preferred embodiment of the instant disclosure includes a system for diagnosing TIA or an acute cerebral event as disclosed elsewhere. Examples of systems include clinical chemistry analyzers, coagulation chemistry analyzers, immunochemistry analyzers, urine analyzers, nucleic acid analyzers, used to detect the result of chemical or biological reactions or to monitor the progress of chemical or biological reactions. More specifically, exemplary systems of the instant disclosure may include Roche Elecsys™ Systems and Cobas® e Immunoassay Analyzers, Abbott Architect™ and Axsym™ Analyzers, Siemens Centaur™ and Immulite™ Analyzers, and Beckman Coulter UniCel™ and Acess™ Analyzers, or the like.

Embodiments of the system may include one or more analyzer units utilized for practicing the subject disclosure. The analyzer units of the system disclosed herein are in operable communication with the computing device disclosed herein through any of a wired connection, Bluetooth, LANS, or wireless signal, as are known. Additionally, according to the instant disclosure, an analyzer unit may comprise a stand-alone apparatus, or module within a larger instrument, which performs one or both of the detection, e.g. qualitative and/or quantitative evaluation of samples for diagnostic purpose. For example, an analyzer unit may perform or assist with the pipetting, dosing, mixing of samples and/or reagents. An analyzer unit may comprise a reagent holding unit for holding reagents to perform the assays. Reagents may be arranged for example in the form of containers or cassettes containing individual reagents or group of reagents, placed in appropriate receptacles or positions within a storage compartment or conveyor. Detection reagents may also be in immobilized form on a solid support which are contacted with the sample. Further, an analyzer unit may include a process and/or detection component which is optimizable for specific analysis.

According to some embodiments, an analyzer unit may be configured for optical detection of an analyte, for example a marker, with a sample. An exemplary analyzer unit configured for optical detection comprises a device configured for converting electro-magnetic energy into an electrical signal, which includes both single and multi-element or array optical detectors. According to the present disclosure, an optical detector is capable of monitoring an optical electromagnetic signal and providing an electrical outlet signal or response signal relative to a baseline signal indicative of the presence and/or concentration of an analyte in a sample being located in an optical path. Such devices may also include, for example, photodiodes, including avalanche photodiodes, phototransistors, photoconductive detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable pre-preamplifiers include, for example, integrating, transimpedance, and current gain (current mirror) pre-amplifiers.

Additionally, one or more analyzer unit according to the instant disclosure may comprise a light source for emitting light. For example, a light source of an analyzer unit may consist of at least one light emitting element (such as a light emitting diode, an electric powered radiation source such as an incandescent lamp, an electroluminescent lamp, a gas discharge lamp, a high-intensity discharge lamp, a laser) for measuring analyte concentrations with a sample being tested or for enabling an energy transfer (for example, through florescent resonance energy transfer or catalyzing an enzyme).

Further, an analyzer unit of the system may include one or more incubation units (for example, for maintaining a sample or a reagent at a specified temperature or temperature range). In some embodiments, an analyzer unit may include a thermocycler, include a real-time thermocycler, for subjecting a sample to repeated temperature cycles and monitoring a change in the amount of an amplification product with the sample.

Additionally, an analyzer unit of the system disclosed herein may comprise, or be operationally connected to, a reaction vessel or cuvette feeding unit. Exemplary feeding units include liquid processing units, such as a pipetting unit, to deliver samples and/or reagents to the reaction vessels. The pipetting unit may comprise a reusable washable needle, e.g. a steel needle, or disposable pipette tips. The analyzer unit may further comprise one or more mixing units, for example a shaker to shake a cuvette comprising a liquid, or a mixing paddle to mix liquids in a cuvette, or reagent container.

It follows from the above that according to some embodiments of the instant disclosure, portions of some steps of methods disclosed and described herein may be performed by a computing device. A computing device may be a general purpose computer or a portable computing device, for example. It should also be understood that multiple computing devices may be used together, such as over a network or other methods of transferring data, for performing one or more steps of the methods disclosed herein. Exemplary computing devices include desktop computers, laptop computers, personal data assistants ("PDA"), such as BLACKBERRY brand devices, cellular devices, tablet computers, servers, and the like. In general, a computing device comprises a processor capable of executing a plurality of instructions (such as a program of software).

A computing device, preferably, has access to a memory. A memory is a computer readable medium and may comprise a single storage device or multiple storage devices, located either locally with the computing device or accessible to the computing device across a network, for example. Computer-readable media may be any available media that can be accessed by the computing device and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or any other memory technology, CD-ROM, Digital Versatile Disk (DVD) or other optical disk storage, magnetic cassettes, magnetic tape, magnetic disk storage or other magnetic storage devices, or any other medium which can be used for storing a plurality of instructions capable of being accessed by the computing device and executed by the processor of the computing device.

According to embodiments of the instant disclosure, software may include instructions which, when executed by a processor of the computing device, may perform one or more steps of the methods disclosed herein. Some of the instructions may be adapted to produce signals that control operation of other machines and thus may operate through those control signals to transform materials far removed from the computer itself. These descriptions and representations are the means used by those skilled in the art of data processing, for example, to most effectively convey the substance of their work to others skilled in the art.

The plurality of instructions may also comprise an algorithm which is generally conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as values, characters, display data, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities. According to some embodiments of the instant disclosure, an algorithm for carrying out a comparison between a determined amount of one or more markers disclosed herein, and a suitable reference, is embodied and performed by executing the instructions. The results may be given as output of parametric diagnostic raw data or as absolute or relative amounts. According to various embodiments of the system disclosed herein, a "diagnosis" may be provided by the computing device of a system disclosed herein based on said comparison of the calculated "amount" to a reference or a threshold. For example, a computing device of a system may provide an indicator, in the form of a word, symbol, or numerical value which is indicative of a particular diagnosis.

The computing device may also have access to an output device. Exemplary output devices include fax machines, displays, printers, and files, for example. According to some embodiments of the present disclosure, a computing device may perform one or more steps of a method disclosed herein, and thereafter provide an output, via an output device, relating to a result, indication, ratio or other factor of the method.

The present invention also encompasses a kit for diagnosing TIA in a subject, said kit comprising at least a detection agent for the NT-proANP polypeptide and, preferably, standards which reflect the reference amounts as derived from a subject known to have exhibited a TIA and/or from a subject known not to have exhibited a TIA:

The present invention also encompasses a kit for diagnosing TIA in a subject, said kit comprising at least a detection agent for the NT-proANP polypeptide, and a detection agent for the NT-proBNP polypeptide and, preferably, standards which reflect the reference ratios as derived from a subject known to have exhibited a TIA and/or from a subject known not to have exhibited a TIA:

The present invention also encompasses a kit for diagnosing an acute cerebral ischemic event in a subject, said kit comprising at least a detection agent for the NT-proANP polypeptide, and a detection agent for the NT-proBNP polypeptide and, preferably, standards which reflect the reference ratios as derived from a subject known to have exhibited an acute cerebral ischemic event or from a subject known not to have exhibited an acute cerebral ischemic event:

The term "kit" as used herein refers to a collection of the aforementioned components, preferably, provided in separately or within a single container. The container also comprises instructions for carrying out the method of the present invention. These instructions may be in the form of a manual or may be provided by a computer program code which is capable of carrying out the comparisons referred to in the methods of the present invention and to establish a diagnosis accordingly when implemented on a computer or a data processing device. The computer program code may be provided on a data storage medium or device such as a optical storage medium (e.g., a Compact Disc) or directly on a computer or data processing device. Moreover, the kit may, preferably, comprise standards which reflect the reference amounts as described and referred to elsewhere herein in detail. The detection agent is, preferably, immobilized on a carrier, and, preferably, a test stripe.

All references cited in this specification are herewith incorporated by reference with respect to their entire disclosure content and the disclosure content specifically mentioned in this specification.

The following Examples shall merely illustrate the invention. They shall not be construed, whatsoever, to limit the scope of the invention.

Example 1: Determination of NT-proBNP and NT-proANP

NT-proBNP was determined using Roche's electrochemiluminescence ELISA sandwich test Elecsys proBNP II STAT (Short Turn Around Time) assay. The test employs two monoclonal antibodies which recognize epitopes located in the N-terminal part (1-76) of proBNP (1-108).

NT-proANP (amino acids 1 to 98 of the pre-proANP peptide) was determined using the NT-proANP assay from Biomedica Medizinprodukte GmbH (Vienna, Austria). The catalogue number. BI-20892. The detection limit is 0.05 nmol/l. The assay makes use of polyclonal sheep anti proANP antibodies.

The level of the biomarkers were tested in serum samples from the following group of subjects
 healthy subjects (n=149)
 patients with stable coronary artery disease CAD (i.e. patients in whom frequently stroke develops, n=235),
 patients with cardiac decompensation (n=64),
 patients with TIA (n=79).
 patients with minor and major stroke (n=61 and 108, respectively)

CAD Patients:

A total of 235 patients with chronic artery disease were included into the study, mean age 64 years, they were 141 males and 94 females. In all patients, coronary artery disease was verified by angiography. A 50% reduction in vessel diameter was used for classification of 1, 2 or 3 vessel disease. Cardiac function was assessed by echocardiography and determination of NT-pro BNP Heart Failure:

A further group of 64 patients has decompensated heart failure (24 women and 40 men, mean age 69 years). They were characterized by increasing shortness of breath in the previous 2 weeks, all patients could be classified as NYHA III or IV according to the NYHA classification.

Healthy Controls:

149 clinically healthy human subjects were included into the study as controls, 52 males and 97 females (median age 41 years, range 19 to 56 years). These subjects had no cardiac disease as assessed by medical history and an electrocardiogram, no diabetes mellitus and no risk factors of these diseases. Moreover they had normal kidney function as assessed by normal creatinine values and malignant disorder.

Stroke/TIA Patients:

A total of 255 patients with TIA or ischemic stroke (mean age 70 years) were included in this study. Transitory ischemic attack was present in 23 patients, minor stroke was diagnosed in 61 patients and major stroke was found in 108 patients. In addition as described above caotoid and transcranial ultrasound as well as electro- and echocardiography were performed and the patients were classified according to the TOAST criteria. In patients with stroke and TIA, the biomarkers NT-proANP and NT-proBNP were measured in samples obtained at presentation as well as in samples obtained six and 24 hours after presentation. The median interval between the onset of symptoms and admission was 4.2 hours (25th percentile: 2.5, 75th percentile: 8 hours).

Example 2: Results

The following results were obtained (indicated are the Median levels, as well as the $25^{th}$ and $75^{th}$ percentile):

|  | NT-pro BNP pg/ml | NT-pro ANP pg/ml |
|---|---|---|
| Healthy subjects N = 149 | 37 18-68 | 882 635-1280 |
| Patients with stable CAD N = 236 | 266 95-928 | 2710 1880-4662 |
| Patients with Cardiac Decompensation N = 64 | 4477 1971-7131 | 33600 12570-57800 |
| TIA: n = 27 | 331 165-473 | 106000 79000-149000 |
| Minor stroke n = 60 | 238 79-547 | 81000 43400-125000 |
| Major stroke (n = 108) | 412 127-1053 | 107151 70600-240000 |

The surprising finding indicated that NT-proANP levels in stroke were significantly increased in patients with TIA and stroke. In particular, they were higher than in overt cardiac decompensation. Thus, NT-proANP separated cardiac patients from stroke patients. The determination of NT-proBNP provides additional information.

Moreover, the ratios of NT-proANP to NT-proBNP were determined:

The ratios were as follows (Median, 25th percentile/75th percentile):

| Healthy | 74 (14/125) |
|---|---|
| CAD | 10 (4/25) |

| | |
|---|---|
| Decompensated HF | 10 (4/18) |
| Major stroke | 249 (128/603) |
| Minor stroke | 321 (149/670) |
| TIA | 524 (204/905) |

As it can be seen from the table, the determination of the ratio is advantageous since it allows for the differentiating between i) patients having risk factors of stroke/TIA, i.e. patients with coronary artery disease (CAD) and patients with heart failure (HF) which have high levels of NT-proANP and NT-proBNP, and ii) patients who have suffered from stroke or TIA.

When NT-proANP values were followed in the course of stroke, the following values were obtained:

| | NT-pro ANP pg/ml |
|---|---|
| At presentation | 106000 |
| | 79000-149000 |
| At 6 hours | 95500 |
| | 54000-139000 |
| At 24 hours | 82000 |
| | 48000-139000 |

Follow up indicated that this was a lasting effect, indicating that also past events could be recognized.

Conclusions:

The recognition of TIA is important as it may precede stroke which is frequently disabling. Frequently TIA lasts only for minutes and most TIAs resolve within one hour without causing permanent damage to the brain. The diagnosis of TIA is difficult as i) TIA mimics a variety other disorders depending on the localisation of TIA and as ii) the patient presents for assessment symptoms are no longer present which makes the final diagnosis difficult. TIA frequently develops in patients with pre-existing heart diseases such as systemic hypertension, coronary artery disease and heart failure of different origin. A surprising finding of this study was that NT-proANP which is known to be released in heart failure is highly elevated in stroke and surprisingly also in TIA even exceeds the levels found in patients with advanced and decompensated heart failure. Also the ratio of NT-proANP/NT-pro BNP can be safely used for this purpose, in particular in heart failure patients.

The clinical importance of confirmation of suspected TIA lies in the identification of the underlying cause (e.g. cardioembolic), the appropriate intervention (angioplasty e.g. in carotis stenosis, anticoagulation in atrial fibrillation) and, thus, in the prevention of stroke and specifically major stroke.

Moreover, it has been shown that the determination of the ratio of NT-proANP/NT-pro BNP allows for a reliable diagnosis of stroke and TIA, in particular in patients suffering from heart failure.

The invention claimed is:

1. A method for diagnosing an acute cerebral ischemic event in a subject who is suspected to suffer from an acute cerebral ischemic event, comprising:
   determining the amount of NT-proANP in a blood, serum or plasma sample from said subject;
   determining the amount of NT-proBNP in a sample from said subject;
   calculating a ratio of the amounts of NT-proANP and NT-proBNP;
   comparing the calculated ratio to a reference ratio, thereby diagnosing the acute cerebral ischemic event based on the comparison of the calculated ratio to a reference ratio;
   wherein the reference ratio is derived from a sample from a subject known to have exhibited an acute cerebral ischemic event, wherein a ratio of NT-proANP to NT-proBNP in the sample from the test subject which is essentially identical to the reference ratio or which is larger than the reference ratio indicates that the subject has exhibited an acute cerebral ischemic event, and/or
   the reference ratio is derived from a sample from a subject known not to have exhibited an acute cerebral ischemic event, and wherein a ratio of NT-proANP to NT-proBNP in the sample from the test subject which is essentially identical to the reference ratio or which is lower than the reference ratio indicates that the subject has not exhibited an acute cerebral ischemic event; and
   treating a patient diagnosed with acute cerebral ischemic event with aspirin, heparin, stenting, anticoagulation therapy, anti-platelet therapy, and/or endarterectomy.

2. The method of claim 1 wherein the subject suffers from heart failure and/or from coronary artery disease.

3. The method of claim 1, wherein the subject who is suspected to have exhibited an acute cerebral event has shown symptoms of an acute cerebral event within 72 hours before the sample has been obtained.

4. The method of claim 1, wherein the subject who is suspected to have exhibited an acute cerebral event has shown symptoms of an acute cerebral event within 24 hours before the sample has been obtained.

5. The method of claim 1, wherein the sample has been obtained later than 1 one hour after the onset of symptoms of the acute cerebral event.

* * * * *